United States Patent
Rizun

(10) Patent No.: US 10,130,656 B2
(45) Date of Patent: Nov. 20, 2018

(54) MINERAL PITCH RESIN MANUFACTURED UNDER A SAFE AND LOW TEMPERATURE PROCEDURE

(71) Applicant: Nodari Rizun, San Diego, CA (US)

(72) Inventor: Nodari Rizun, San Diego, CA (US)

( * ) Notice: Subject to any disclaimer, the term of this patent is extended or adjusted under 35 U.S.C. 154(b) by 370 days.

(21) Appl. No.: 15/089,372

(22) Filed: Apr. 1, 2016

(65) Prior Publication Data

US 2016/0213713 A1 Jul. 28, 2016

Related U.S. Application Data

(63) Continuation-in-part of application No. 13/856,440, filed on Apr. 4, 2013, now abandoned.

(60) Provisional application No. 61/636,008, filed on Apr. 20, 2012.

(51) Int. Cl.
*A61K 35/02* (2015.01)
*A61J 1/05* (2006.01)

(52) U.S. Cl.
CPC ............... *A61K 35/02* (2013.01); *A61J 1/05* (2013.01)

(58) Field of Classification Search
None
See application file for complete search history.

(56) References Cited

U.S. PATENT DOCUMENTS

| | | |
|---|---|---|
| 2013/0280291 A1 | 10/2013 | Rizun |
| 2016/0213713 A1 | 7/2016 | Rizun |

FOREIGN PATENT DOCUMENTS

RU 2055585 C1 3/1996

OTHER PUBLICATIONS

International Search Report and Written Opinion for PCT Application No. PCT/US2017/019517, dated May 19, 2017 in 10 pages.
Sharma et al., "Shilajit: evaluation of its effects on blood chemistry of normal human subjects", Ancient Science of Life (2003) 23(2):114-119.
Tran, "Mumio: natural pharmaceutical material", Bachelor thesis, Tomas Bata University in Zlin, Faculty of technology, (2014) [Retrieved from the internet on Apr. 10, 2017 <URL:http://digilib.k.utb.cz/bitstream/handle/10563/30838/tran_2014_dp.pdf?sequence=1>, in 20 pages.

*Primary Examiner* — Susan Hoffman
(74) *Attorney, Agent, or Firm* — Procopio, Cory, Hargreaves & Savitch LLP; Lisel M. Ferguson

(57) ABSTRACT

A manufacturing method of mineral pitch resin, which comprises the steps of identification of the mineral, collection of the mineral, and processing of the mineral in a temperature controlled clean room facility by dissolving, filtering and demoisturizing. This method produces a resin which is verifiably free from harmful contaminants and is safe for humans to consume as a healing, tonifying and adaptogenic substance.

14 Claims, 2 Drawing Sheets

MINERAL PITCH RESIN MANUFACTURED UNDER A SAFE AND LOW TEMPERATURE PROCEDURE

CROSS REFERENCE TO RELATED APPLICATIONS

This application is a Continuation-in-Part of U.S. application Ser. No. 13/856,440, filed Apr. 4, 2013, now abandoned, which claims the benefit of U.S. Provisional Application No. 61/636,008, filed Apr. 20, 2012, the contents of which are incorporated herein by reference in their entirety.

FIELD OF THE INVENTION

The present invention relates, in general, to a method of manufacture for mineral pitch resin. More particularly, the present invention relates to a method which comprises the steps of identification of the material, collection of the material, and a multi-step processing of the material for human consumption as a healing, tonifying and adaptogenic substance.

DETAILED DESCRIPTION OF THE INVENTION

Embodiments described herein are directed to a method for extracting raw mineral pitch resin from naturally found sources and then utilizing a multi-step processing method to manufacture the same so that it is virtually free from harmful contaminants and is safe for humans to consume as a healing, tonifying and adaptogenic substance.

The first step is to find and identify the raw material known as mineral pitch also called shilajit, mumie, or salajeet. This pitch is found in stones in several mountainous areas of the world. Some areas in the world in which this mineral pitch is found are Caucasus, Altai, Himalayas, Siberia, Mongolia, and Antarctica.

The stones are found in proximity to mountain slopes facing the sunny side with proximity of vegetation within one to five (1-5) kilometers. Such stones or formations can be found in the mountain crevices, caves, and the raw resin deposits sometimes may have an appearance of dark gooey matter oozing out of rocks. Visually the raw resin deposits may appear as a part of the crevice, but if extracted may be 1 to up to 150 cm in diameter, and are mixed with surrounding rock, sand, pebble, residuals of local plants.

Measuring the identified raw material is done with simple measuring tape or a ruler. To measure the depth of how deep the deposit in the stones are in a crevice or a rock is performed by a measuring rod with a scale on it, which allows to identify the depth of the stone. The color of the raw material can range from very dark brown, to red, yellow and shades of white. So shades or inclusions of white are important as the white indicates that microorganisms beneficial to the raw material will be properly populated and processed the matter. Such microorganisms include simple yeasts and aerobic bacteria, which creates multiple metabolites that give the resin its health properties.

In order to determine if the raw material is suitable it is first tested in the field. In order to be suitable for collection the material must contain 1-50% glycine. Once the raw material is identified the exterior layer is grated off, then a selected amount of raw material is taken for testing. The collected raw material is mixed in predetermined quantities with water and triketohydrindene monohydrate. A referred ratio for testing the raw material is one part raw material to one part monohydrate to eight parts water. The mixture is boiled for 5-30 min and cooled down for 5-30 min., the solution once settled fully 5-30 min has a color ranging from blue to purple. The ideal raw material has a color in the blue violet range as this shows a good amount of glycine. This basic initial test suffices for identification of glycine as well as other naturally occurring in the raw material amino acids. Later, once the material has been harvested and processed, the presence of Glycine is reconfirmed with more accurate quantitative and qualitative methods which include High-Performance Liquid Chromatography (HPLC) or infrared (IR) spectrography or any conventional United States Pharmacopeial Convention (USP) accepted method. At this stage the raw material is deemed suited for collection and further processing. The raw material is simply picked by hand or extracted with pickaxes or any firm objects that may separate if from the rock, stone or the location.

Once the raw material is identified, the external layers are removed with a sharp object like a chisel or a grater or any object with similar or identical functions. The external layer of the raw material is removed "grated" off to the depth ranging from 1 up to several centimeters. The depth of external layer removal can be measured with a simple ruler or any device that resembles a ruler. The external layer is removed before collection as it contains impurities. Once the external layers are removed the material is very briefly washed off or placed into food grade alcohol.

Once collected the raw resin material is placed in a thermos-electric cooler, which maintain internal temperatures lower than 48 degrees Celsius. The coolers with the material are transported to a facility where the air is continuously purified of environmental pollutants, airborne microbes, dust particles, aerosol particles, and any chemical vapors. In this controlled manufacturing environment, or clean room, the air at any time adjacent to the resin has either no particles in the air or anywhere ranging from 10 up to maximum 100000 ranging in size from less than 0.1 to 5 micrometers in sized. This is achieved through controlled enclosures and proper air filtration. The temperature at this manufacturing space is always kept lower than 48 degrees Celsius.

The material is removed from the thermo-controlled containers already in an air and temperature controlled environment as described above, also called a clean room. Once removed from the containers the raw resin material is briefly washed off or immersed in up to 99% percent pure $CH_3CH_2OH$ in possible combination with $H_2O$.

Further dissolution and filtering of the previously qualified material takes place. The material is dissolved in preliminary treated water. In order to dissolve the material containing the raw resin it is agitated. Such water is considered sterile and contains less than 0.25 USP Endotoxin unit per ml. with any microscopically detectable particles absent. Initially the water contains under 0.1 PPM of dissolved solids. The material is combined with water in proportions necessary to turn the combination into a free flowing liquid.

Different types of water can be used depending on the type of processed resin which is desired. Minerals, herbal extracts and biologically active substances may be added to the water. The water used may be from sources from specific locations which were previously global positioning system (GPS) identified, the water can be passed through a magnetic field of 1 to 20000 Gauss, exposed to sound frequencies from 0.1 to 440 HZ. Combination of material to water ranges but generally based on the density of the initial material may be 1:1, 1:2, 1:3, or higher levels of water. The raw resin material is further dissolved by letting it dissolve passively or agitating it mechanically with any immersed tool that moves at speeds less or equal to 0.1 rpm and above.

Next the solution is filtered through multiple size filters, as a rule higher pore size to smaller pores size. Filters will range from several millimeters down to several microns. This procedure eliminates undesired pebble, sand, sediment, fiber, and large particles. Eventually the solution will pass passively or under pressure through a filter with a pore size equal or possible even less than 0.03 microns. This allows for the filtrate to come out that later will result into manufacturing of highly bioavailable resin, with particles eliminated, which cannot be easily absorbed by the human body. This procedure requires pressure in order to properly filter out the particles not desired due to the lack of bioavailability and manage the production time for the resin. The pressure will be produced either mechanically by a piston or similar device, or gas such as compressed air. Pressure in such case will be sufficient to effectively push the solution through the numerous filter, the pressure with be equal (passive) or above 1 psi and will range generally up to 14.7 psi but may be higher if the technical capability permits. The process may be repeated up to 50 times.

At any stage of the filtration process, prior or after, herbal extracts or minerals can be added to the solution. The extract may be of any plant that is beneficial to human health. The extract could also be a mineral beneficial to human health. Due to the fact that the resin improves effect of herbs on the body is it beneficial to combine the resin and the herbal extracts. Extracts can be received through different processes, the can be introduced in form of liquid, solid and semisolid extracts to the resin. It is important that the extracts are clearly identified for active ingredients and their levels of actives. This is done separately through any conventionally recognized process described in USP or any other pharmacopeia monographs or technical literature. Such extracts may be received either through simple extraction of liquids, oils, or resins of the herb or through any recognized process such as infusion, decoctions, maceration, digestion, expression, percolation, enfleurage, oil expression, steam distillation, solvent extraction, fractional distillation, phytonic extraction, microorganism and gas type of extractions. Minerals also obtained through any conventional and described in USP or any other process or pharmacopeia or technical process may be added. The material is filtered from 2 to 50 times in order to remove all of the impurities.

After the final stage of filtration the actual resin is made through removal of moisture from the filtrate. The solution is churned or left idle during the process with or without the occasional churning. The vessel with the resin may be actively (by contact) or passively (leaving by a heat source) heated to allow the moisture escape from the solutions and concentrate it to a solid or a semisolid. In order to speed up the removal of moisture one may introduce an air flow from any source just ensure that the moisture can escape from the filtrate into the air or a special space. Another method to remove the excess moisture is vacuum. The vessel with resin is placed a vacuum chamber, where the vacuum is less than 1 atmosphere or 760, the vessel may be heating, and the resin may be slowly churned or mechanically agitated. The moisture will escape leaving the resin. Moisture can be measured at any time with a basic moisture meter equipped with a moisture sensor methods that can be used as gravimetric, coulometric, microwave resonance, Karl Fischer, infrared, conductive. The final resin will have a moisture level of between 1 and 25 percent.

During the whole manufacturing process the temperature will be maintained lower than 39 degrees Celsius. This can be measured through very simple thermometer devices with temperature sensors for air, liquid and semisolids.

The resulting processed resin will be a high quality and pure mineral pitch, with levels of impurities of less than 3% of the total mass. This level of undesirable contaminants is lower than majority of traditionally manufactured shilajit, mumie or any form of mineral pitch. The processed resin will also have a higher efficacy due to higher bioavailability due to very small size of the resin forming particles. Now that the resin is processed it will be tested for the levels of residual or absence of the contaminant levels, microbiological safety, moisture levels by mass ashes not soluble in 10% HCl acid, ashless humic acids and glycine. It is tested by using USP testing procedures or other Pharmacopeia method.

Resulting resin resulting from a properly conducted manufacturing process will have indicator equal or better than the following:

For Lead: 3 mg/kg
For Arsenic: 6 mg/kg
For Cadmium: 0.5 mg/kg
For mercury: 1 mg/kg
For microbiological pathogens: less than 10 GFU/g
Moisture Levels by mass: 0.001 up to 60%
Ashes not soluble in 10 HCl: 1.6%
Ashless humic acids: no less than 5%
Glycine: no less than 1%

Once the resulting solid or semisolid resin passes or is better than the above stated criteria. It can be repackaged in of either transportation or individual distribution. For transportation the resin is packaged in containers that are completely opaque to light. In such state with no penetration of light the resin is in a "dormant" state and will indefinitely store and can be transported for an indefinitely long time. (wholesale packaging first phase)

The second method of packaging is in the biophotonic glass. Biophotonics improves the properties of nutritives and will substantially improve the quality of the resin. Such glass with allow the permeation of the spectrum of light within the wavelength of 315 to 450 nm, and frequency of the 668-789 THz, it also blocks the light in the spectrum of 450 to 620 nm, and allows the light through in the range of 620 to 750 nm. At this point the resin can be stored indefinitely and will be stable over indefinite period of time.

BRIEF DESCRIPTION OF THE FIGURES

The accompanying figures, which are incorporated in and constitute a part of the specification, illustrate embodiments of the invention and, together with the description, serve to explain the objects, advantages, and principles of the invention. In the drawings.

DETAILED DESCRIPTION OF PREFERRED EMBODIMENTS

After reading this description it will become apparent to one skilled in the art how to implement the invention in various alternative embodiments and alternative applications. However, all the various embodiments of the present invention will not be described herein. It is understood that the embodiments presented here are presented by way of an example only, and not limitation. As such, this detailed description of various alternative embodiments should not be construed to limit the scope or breadth of the present invention as set forth below.

Figure 1:
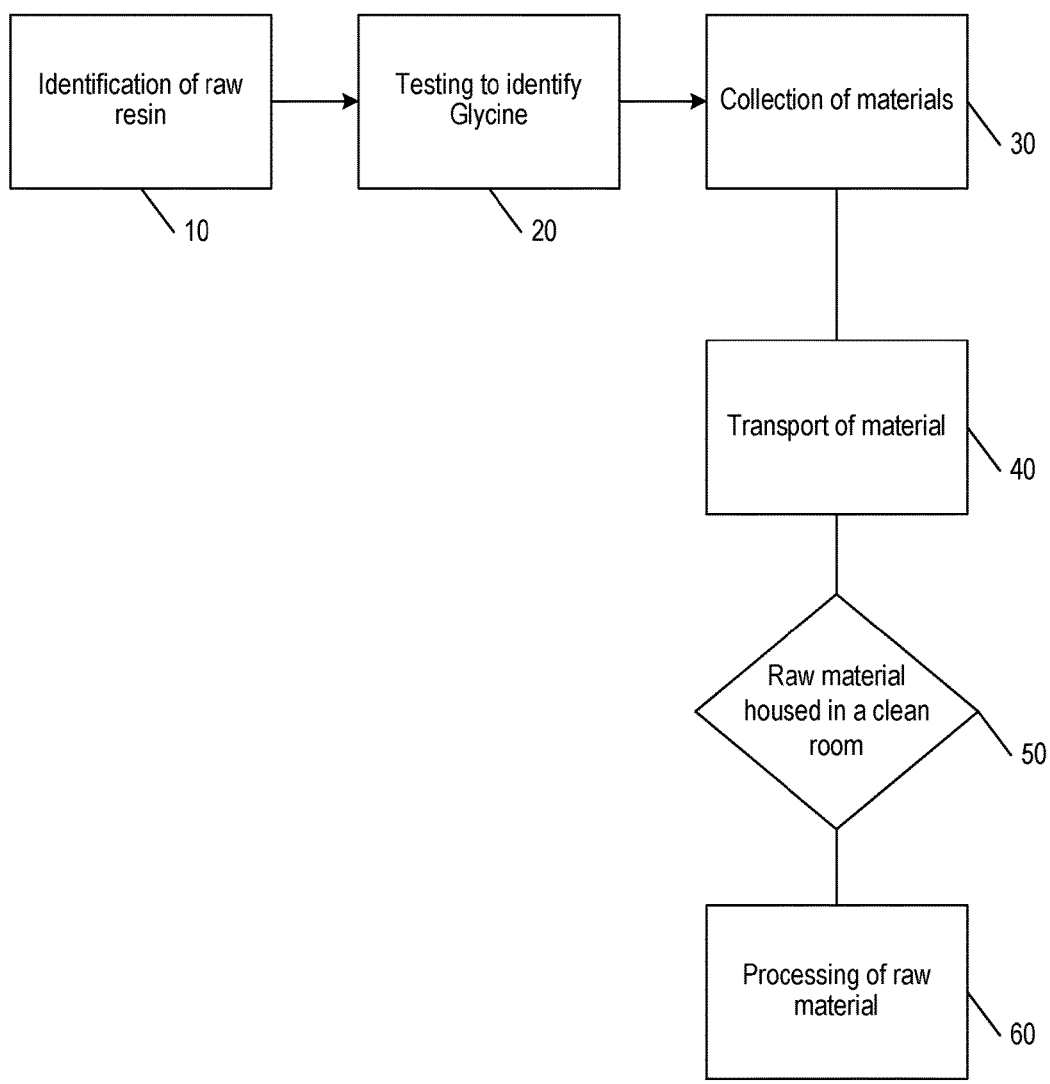
FIG. 1 is a flow diagram which shows the steps in the method of creating resin for human consumption.

With reference to FIG. 1, a flow diagram showing the main steps of the method for identifying, collecting and processing raw mineral resin is shown. First, the raw resin material must be identified at step 10. The raw material known as mineral pitch is found in stones in several mountain areas of the world. The stones are found in proximity to mountain slopes facing the sunny side with a proximity of vegetation within 1-5 kilometers. Once the raw material is identified, the deposit size is measured with a tape or a ruler. The color of the raw material identified at step 10 can range from very dark brown to red, yellow and shades of white. Shades and inclusion of white are important indicators that the beneficial microorganisms are present in the raw material. Beneficial microorganisms include simple yeasts anaerobic bacteria, which create multiple metabolites that give the resin its health properties.

Once the raw material is identified the next step in the process is to collect a small portion of the resin and test it in the field, step 20. If the tests determine that the material contains 10-50% glycine, it will be suitable for collection. In order to test the raw material the exterior layer is first grated off. Then a selected amount of raw material is taken for testing. The collected raw material is mixed with water and triketohydrindene monohydrate. The preferred ration of material for testing at step 20 is one part raw material, one part monohydrate to eight parts water. Once the mixture is combined it is boiled for 5-30 minutes and then cooled down for an additional 5-30 minutes. Once the material has settled it should have a color ranging from blue to purple. The ideal raw material has a color in the blue to violet range which shows a good amount of glycine. The amount of glycine will later be confirmed once the material has been transported to the clean room.

Once the material has been tested and has been confirmed to contain 10% to 50% glycine it is collected, step 30. The first step in the collection is to remove the external layers of the raw resin with a sharp object like a chisel or grater or any object with similar functionality. The external layer of the raw material is removed or grated off to a depth ranging from one to up to several centimeters. This external layer is then discarded and the underlying material is collected by being picked by hand or extracted with pick axes or other firm objects that may separate it from the rocks or stones in the collection location. Once the material is extracted it is briefly washed off and placed in to food grade alcohol.

The next step in the process is the transport of the material at step 40. The collected washed raw material is placed in a thermo-electric cooler, which maintains an internal temperature lower than 48 degrees Celsius. The coolers with the material are transferred to a facility where air is continuously purified of environmental pollutants, airborne microbes, dust particles, aerosol particles, and any chemical vapors. Such a room is called a clean room. The transport occurs in the thermo-electric coolers and the material is not released from these coolers until it is in to the clean room and the clean room is sealed. In the clean room the air at any time adjacent to the resin has either no particulates in the air or any particulates ranging from 10 up to a maximum of 100,000 in size from less than 0.1-5 micrometers in size. Such a clean room environment is achieved through controlled enclosures and proper air filtration. The temperature at these locations is always kept lower than 48 degrees Celsius.

At step 50 the material is held in the clean room until it is further processed. At step 60 the processing of the raw material commences and takes place in the clean room. At this stage the raw material is removed from the thermo-controlled containers. Once the material is removed from the containers the raw resin material is briefly washed of or immersed in up to a 99% pure $CH_3CH_2OH$ in possible combination with water $H_2O$.

Figure 2:
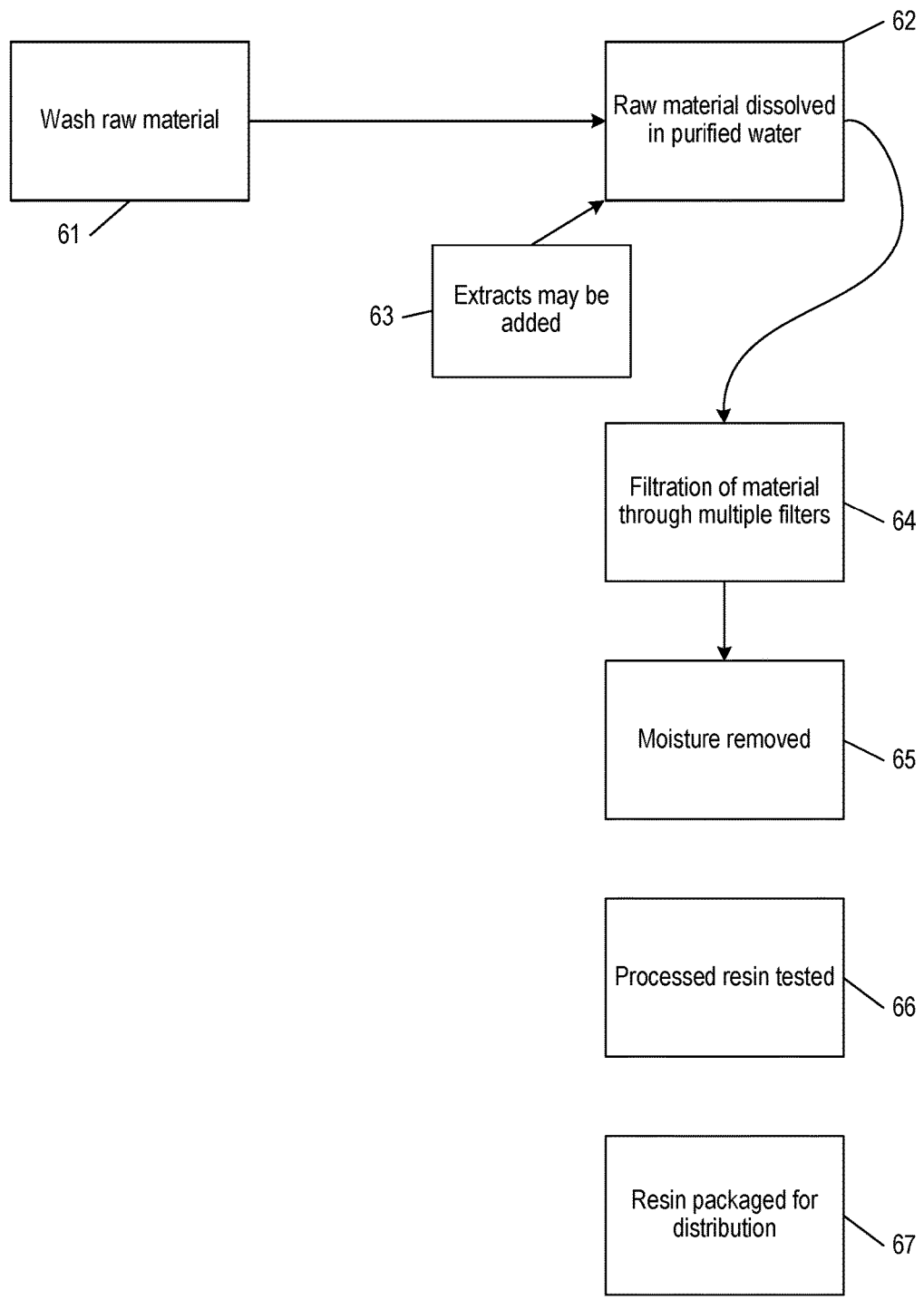
FIG. 2 is a flow diagram which shows the multi-step processing of raw resin to processed resin.

Referring to FIG. 2 in multi-step processing of the raw material now commences so that the raw material may be formed in to processed material for distribution for human consumption. The raw material is first washed off as set forth above, step 61. Next the raw material is dissolved in preliminarily treated water at step 62. The water in which the resin is dissolved is sterile and contains less than 0.25 USP endotoxin unit per ml. with any microscopically detectable particles absent. The water prior to being added to the raw material contains under 0.1 ppm of dissolved solids. The material is combined with the water in proportions necessary to turn the combination in to a free flowing liquid. In order to dissolve the raw material in the water it must be agitated. Depending on the consistency of the raw material this agitation can vary in length and frequency.

Different types of water can be used depending on the type of processed resin which is desired. Minerals, herbal extracts and biologically active substances may be added to the water. The water used may be from sources from specific locations which were previously global positioning system (GPS) identified, the water can be passed through a magnetic field of 1 to 20000 Gauss, exposed to sound frequencies from 0.1 to 440 HZ. Combination of material to water ranges but generally based on the density of the initial material may be 1:1, 1:2, 1:3, or higher levels of water. The raw resin material is further dissolved by letting it dissolve passively or agitating it mechanically with any immersed tool that moves at speeds less or equal to 0.1 rpm and above.

Once the material has been dissolved it will be filtered at step 64. However if desired extracts may be added to the raw material at step 63. These herbal extracts or minerals can be added to the solution at this dissolved stage 62 or could be added later at stages 64 or 65. The extracts which may be added to the resin may be of any plant that is beneficial to human health. The extract could also be a mineral beneficial to human health. Since the resin improves the effects of herbs on the body it is beneficial to combine the resin and herbal extracts to achieve certain desired results. The extracts added to the resin can be obtained through different processes and can be introduced in the forms of liquid, solid or semi-solid extracts. The extracts must be identified for active ingredients and the levels of active ingredients must be tested to confirm they meet the desired requirements. Testing the extracts can be done through any process described in the USP or any other pharmacopeia monograph or technical literature. Such extracts may be collected either through simple extraction of liquids, oils, or resins of the herb or through any recognized process such as infusion, decoction, maceration, digestion expression, percolation, oil expression, steam distillation, solvent extraction, fractional distillation, botanic extraction, microorganism and gas type of extraction.

At the next stage of processing step 64 the raw material dissolved in purified water, either with or without extracts, is filtered from 2 to 50 times to remove all of the impurities. The filtration at step 64 takes place using multiple sized filters. As a standard rule is utilization of the higher pore size filers first and moving toward using smaller pore size filters at successive filtration times. The filters will range from several millimeters down to several microns. In order to push the liquid through the filters pressure may be used. Eventually the solution will pass with pressure through a filter with a pore size equal or possibly even less than 0.03 microns. This filtration process eliminates undesired pebbles, sands, sediments, fiber and larger particles. The pressure used to push the liquid solution through the smaller filters is produced either mechanically by piston or a small similar device or a gas such as compressed air. The pressure to be utilized in such case will be sufficient to effectively push the solution through numerous filters.

After the filtration process at step 64 is complete the moisture is removed at step 65. The liquid with the resin is placed in to a vessel and is either actively or passively heated to allow the moisture to escape from the solution and the concentrate to become a solid or semi-solid. In order to speed up the removal of moisture one may introduce airflow from any source, however the moisture must be able to escape from the filtrate into the air or special space. An alternate method to remove the moisture at step 65 would be to employ a vacuum. In this method the vessel with the resin is placed in a vacuum chamber where the vacuum is less than one atmosphere or 760 torr. In order to speed up this process the vessel might also be being heated and the resin may be slowly churned or mechanically agitated. Once the moisture has been released from the resin it will be a semi-solid or paste and is tested to determine its moisture level. The moisture sensor methods that can be used are gravimetric, coulometric, microwave resonance, Karl Fischer, infrared, conductive. The final resin should have a moisture level of between 1 and 25% of the mass of the product. During the entire manufacture process the temperature of the resin material should be maintained at a temperature of less than 39 degrees Celsius.

Once the moisture is removed at step 65 the processed resin is then tested, at step 66. The resin is tested by using USP testing procedures or other pharmacopeia method. The resulting resin from a properly conducted manufacturing process will have indicator equal or better than the following:

For Lead: 3 mg/kg
For Arsenic: 6 mg/kg
For Cadmium: 0.5 mg/kg
For mercury: 1 mg/kg
For microbiological pathogens: less than 10 GFU/g
Moisture Levels by mass: 0.001 up to 60%
Ashes not soluble in 10 HCl: 1.6%
Ashless humic acids: no less than 5%
Glycine: no less than 1% the resulting solid or semi-solid processed resin passes or is better than the above stated criteria it will be packaged for distribution at step 67.

At step 67 the processed resin is packaged. The processed resin is packaged in containers which do not allow light to penetrate through the walls and make contact with the resin. Once the resin is contained in containers which do not allow light through, it remains in a "dormant" state and will indefinitely store and can be transported for an indefinitely long time. In one embodiment the method of packaging is in biophotonic glass. Biophotonics improves the properties of nutrients and will substantially improve the quality of the resin. Such glass will allow the permeation of the spectrum of light within the wave lengths of 315-415 nanometers, and frequency of the 668-789 thz, it also blocks the light in the spectrum of 450-620 nanometers which allows the light through the range of 620-750 nanometers. This glass thus blocks light in the frequency range which has a negative impact on the resin, but allows light which is in a positive frequency range to penetrate the glass.

Once the resin is packaged it is ready to be distributed for sale to the public and for human consumption. The resulting processed resin is considered the latest and most modern generation of mineral pitch resin for human consumption, also known as shilajit, mumie, salajeet, brag-shun, and other regional names (etc.). This resin has a much higher bioavailability, wider range of preserved nutrient and metabolites, and purity, resulting resin will deliver improved and wider range of benefits, compared to any mineral pitch previously manufactured. The resin can be classified as an adaptogen, regenerative adaptogen, biogenic stimulator, and an adaptogenic delivery system for botanicals. This processed resin is an exceptional nootropic and a natural anxiolytic. It will promote and improve brain functions, specifically memory and concentration, and effectively and healthy will neutralize stress and anxiety. The resin will greatly speed up regenerative processes in the hard and soft tissues in the body, stimulate proliferation of healthy stem cells, regenerate organs and gland, while regenerating their natural and healthy function. This resin stimulates healthy anti-inflammatory and immune response and improves efficacy of herbal formulations. It will enhance mental and physical performance. Normalize healthy function of bone marrow and hematopoiesis post radiation exposure. The resin will not only have all combined benefits of all regional resins (ex. Shilajit, mumie, etc.), it will also show unique properties to improve health. Another unique property of the processed resin is an ability to normalize healthy neurochemistry and homeostasis and as a result counter additions to sugar, alcohol, cannabis, opioids, heroin, cocaine and pain medications. Further the resin will promote healthy and effective sleep cycle.

What is claimed is:

1. A method of manufacturing a resin product comprising:
   identification of a raw mineral pitch material;
   collecting the raw material after cutting, grating or shaving off an external layer of the identified raw mineral pitch material;
   testing the collected raw material for glycine;
   washing the collected raw material with food grade alcohol to form a washed material and placing it in thermo-controlled containers;
   transporting the washed material into a clean room facility for processing where the temperature is less than 48 degrees celsius;
   removing the washed material from the thermo controlled container in the clean room facility;
   dissolving the washed material in sterile liquid to create a solution;
   filtering the solution through multiple filters result a filtered solution;
   mixing the filtered solution and dehumidifying and de-moisturizing it so that it turns into a resin or paste form; and
   transferring the resin or paste into transportation containers which isolate the resin from light and the external environment.

2. The method of claim 1, wherein the thermo-controlled container includes a UV sterilization light.

3. The method of claim 1, further comprising filtering the solution up to 50 times.

4. The method of claim 1, further comprising mixing the filtered solution with herbal extracts or other minerals.

5. The method of claim 1, wherein the temperature for processing is less than 39 degrees Celsius.

6. The method of claim 1, wherein the thermos controlled containers are equipped with a source of disinfection.

7. The method of claim 1, wherein the filtering and mixing steps take place in vacuum under pressure.

8. The method of claim 1, wherein the resin is repackaged by transferring it from the transportation containers into individual, glass containers.

9. A method of manufacturing a mineral pitch resin product comprising:
   identification of a raw mineral pitch material;
   collecting the raw material after cutting, grating or shaving off an external layer of the raw identified mineral pitch material;
   washing the collected material with food grade alcohol to form a washed material and placing it in thermo-controlled containers;
   transporting the washed material into a clean room facility for processing where the temperature is less than 48 degrees celsius;
   removing the washed material from the thermo-controlled container in the clean room facility;
   dissolving the washed material in sterile liquid to create a solution;
   filtering the solution through filters to result in a filtered solution;
   mixing the filtered solution and dehumidifying and de-moisturizing it so that it turns into a resin or paste form;
   transferring the resin or paste into transportation containers which isolate the resin from light and the external environment;
   testing the resin to determine a concentration of at least of lead, arsenic, cadmium, mercury, and glycine; and
   repackaging the resin from the transportation containers into individual, glass containers.

10. The method of claim 9, wherein the thermo-controlled containers include a UV sterilization light.

11. The method of claim 9, further comprising filtering the solution up to 50 times.

12. The method of claim 9, further comprising mixing the filtered solution with herbal extracts or other minerals.

13. The method of claim 9, wherein the temperature for processing is less than 39 degrees Celsius.

14. The method of claim 9, wherein the thermo-controlled containers are equipped with a source of disinfection.

* * * * *